United States Patent
Hanebuchi

(10) Patent No.: US 9,351,638 B2
(45) Date of Patent: May 31, 2016

(54) HAND-HELD OPHTHALMOLOGICAL DEVICE

(75) Inventor: Masaaki Hanebuchi, Aichi (JP)

(73) Assignee: NIDEK CO., LTD., Gamagori-shi (JP)

( * ) Notice: Subject to any disclaimer, the term of this patent is extended or adjusted under 35 U.S.C. 154(b) by 167 days.

(21) Appl. No.: 14/362,680

(22) PCT Filed: Dec. 27, 2011

(86) PCT No.: PCT/JP2011/080352
§ 371 (c)(1),
(2), (4) Date: Aug. 13, 2014

(87) PCT Pub. No.: WO2013/098981
PCT Pub. Date: Jul. 4, 2013

(65) Prior Publication Data
US 2014/0375952 A1    Dec. 25, 2014

(51) Int. Cl.
| | |
|---|---|
| *A61B 3/10* | (2006.01) |
| *A61B 3/12* | (2006.01) |
| *A61B 3/103* | (2006.01) |
| *A61B 3/00* | (2006.01) |
| *A61B 3/14* | (2006.01) |

(52) U.S. Cl.
CPC .............. *A61B 3/1208* (2013.01); *A61B 3/0008* (2013.01); *A61B 3/103* (2013.01); *A61B 3/1035* (2013.01); *A61B 3/14* (2013.01)

(58) Field of Classification Search
CPC .................................................... A61B 3/1208
USPC ........................ 351/218, 216, 221, 211, 246
See application file for complete search history.

(56) References Cited

U.S. PATENT DOCUMENTS

| | | | | |
|---|---|---|---|---|
| 5,528,323 A | * | 6/1996 | Fujieda | A61B 3/103 351/211 |
| 5,646,709 A | * | 7/1997 | Carter | A61B 3/145 351/205 |
| 5,859,687 A | * | 1/1999 | Heine | A61B 3/1208 351/216 |
| 6,630,951 B1 | | 10/2003 | Suzuki | |
| 2008/0309877 A1 | | 12/2008 | Saito et al. | |

FOREIGN PATENT DOCUMENTS

| | | |
|---|---|---|
| JP | A-6-46999 | 2/1994 |
| JP | A-11-19039 | 1/1999 |
| JP | A-2000-69353 | 3/2000 |
| JP | A-2001-161644 | 6/2001 |

(Continued)

OTHER PUBLICATIONS

International Search Report issued in PCT/JP2011/080352 mailed Jan. 31, 2012.

*Primary Examiner* — Hung Dang
(74) *Attorney, Agent, or Firm* — Oliff PLC

(57) ABSTRACT

A hand-held ophthalmological device includes: a main unit having an ophthalmoscopic optical system configured to project ophthalmoscopic light to an examinee's eye and receive reflection light therefrom to examine or measure an examinee's eye; a detector placed in the main unit and configured to detect a relative deviation between an optical axis of the ophthalmoscopic optical system and the examinee's eye; a deviation compensating optical system placed as a part of the ophthalmoscopic optical system and configured to compensate the deviation; and a drive part configured to drive the deviation compensating optical system based on output from the detector.

20 Claims, 9 Drawing Sheets

(56) References Cited

FOREIGN PATENT DOCUMENTS

| JP | 2003-189221 A | 7/2003 |
| JP | 2006-071743 A | 3/2006 |
| JP | A-2008-197323 | 8/2008 |
| JP | A-2008-307104 | 12/2008 |
| JP | A-2011-164321 | 8/2011 |
| JP | A-2012-10952 | 1/2012 |

* cited by examiner

HAND-HELD OPHTHALMOLOGICAL DEVICE

CROSS-REFERENCE TO RELATED APPLICATIONS

This is a national phase application based on the PCT International Patent Application No. PCT/JP2011/080352 filed on Dec. 27, 2011, the entire contents of which are incorporated herein by reference.

TECHNICAL FIELD

The present invention relates to a hand-held ophthalmological device for performing examination and measurement of an eye.

BACKGROUND ART

As an ophthalmological device for measuring and examining eyes, there are known an auto-refractometer and a fundus camera, for example. These devices include a floor-standing type device installed in an examination room and a portable hand-held type device (see Patent Document 1).

In the case of the floor-standing type device, this device is wholly moved in three dimensions by an operation member such as a joystick. Such a device is heavy and stable and thus provides relatively high operability for alignment. However, this device is hard to move.

RELATED ART DOCUMENTS

Patent Documents

Patent Document 1: JP-A-11(1999)-19039

SUMMARY

On the other hand, in the case of the hand-held type device, an examiner holds the whole device and moves it three-dimensionally. This device may be moved with respect to an eye due to hand shake or minute movement of the examiner. From this viewpoint, it is conventionally difficult to make alignment of the hand-held type ophthalmological device, which is apt to cause measurement/examination errors.

The present invention has been made to solve the above problems and has a purpose to provide a hand-held ophthalmological device capable of providing high operability and performing stable measurement and examination.

To achieve the above purpose, one aspect of the invention provides a hand-held ophthalmological device includes: a main unit having an ophthalmoscopic optical system configured to project ophthalmoscopic light to an examinee's eye and receive reflection light therefrom to examine or measure an examinee's eye; a detector placed in the main unit and configured to detect a relative deviation between an optical axis of the ophthalmoscopic optical system and the examinee's eye; a deviation compensating optical system placed as a part of the ophthalmoscopic optical system and configured to compensate the deviation; and a drive part configured to drive the deviation compensating optical system based on output from the detector.

EFFECTS OF THE INVENTION

The invention can provide high operability and perform stable measurement and examination.

MODE FOR CARRYING OUT THE INVENTION

Summary

An ophthalmological device in a present embodiment is a hand-held ophthalmological device including a main unit, a detector to detect a displacement, a displacement compensating optical system, and a drive part to drive the displacement compensating optical system.

The main unit has an ophthalmoscopic optical system. This ophthalmoscopic optical system is provided to project ophthalmoscopic light to an eye E and receive reflection light therefrom to examine or measure the eye E. The ophthalmoscopic optical system is an ophthalmoscopic optical system configured for example to project a measurement index to an eye to be examined and receive reflection light therefrom through a light receiving element to thereby measure ophthalmic optical characteristics of the eye. Typical examples of such a device are an auto-refractometer and a keratometer. The ophthalmoscopic optical system may be a photographing optical system (e.g., a fundus camera, an ophthalmic OCT) to photograph an image of an eye.

The detector to detect a displacement is placed in the main unit and provided to detect a relative positional displacement between an optical axis of the ophthalmoscopic optical system and the eye E. In this case, it is more effective that the detector is configured to optically detect the relative positional displacement between the optical axis of the ophthalmoscopic optical system and an anterior segment of the eye. For instance, there are provided a projection optical system configured to form an index image at a position corresponding to a nearly corneal apex of the eye E and an optical position sensor is provided to detect the position of reflection light of the index image. Based on a light reception signal from the optical position sensor, a relative displacement between the optical axis of the ophthalmoscopic optical system and the eye E in a direction perpendicular to the optical axis of the ophthalmoscopic optical system is detected at high speed.

An effective one as the detector is, for example, a deviation detector to detect a relative deviation (first displacement) between the optical axis of the ophthalmoscopic optical system and the eye E. This deviation includes a deviation applied to the main unit (shake or minute movement of an examiner's hand) and a deviation caused by the movement of an examinee. Conceivable configurations as the detector are for example an angular velocity sensor, an acceleration sensor, and others configured to detect a deviation applied to the main unit, and also a light receiving sensor (e.g., an optical position sensor, an imaging element) configured to receive reflection light from an eye (e.g., a cornea), an ultrasonic sensor, and others. In this case, an effective one is a shift deviation detector to detect a shift deviation applied to the main unit.

The aforementioned detector may be configured to detect a displacement (second displacement) caused when the eye E is displaced from the optical axis of the ophthalmoscopic optical system. As this detector, for example, there are conceived a light receiving sensor (e.g., an optical position sensor, an imaging element) configured to receive reflection light from an eye (e.g., a cornea), an ultrasonic sensor, and others.

The aforementioned detector may also be configured to detect both the first displacement and the second displacement. As this detector, for example, there are conceived a light receiving sensor (e.g., an optical position sensor, an imaging element) configured to receive reflection light from an eye, an ultrasonic sensor, and others.

The compensating optical system is placed as a part of the ophthalmoscopic optical system and configured to compensate or correct a relative positional displacement between the optical axis of the ophthalmoscopic optical system and the eye E. This compensating optical system is used to compensate a detected positional displacement based on output from the aforementioned detector. It is effective that the deviation compensating optical system is configured to compensate a relative deviation between the optical axis of the ophthalmoscopic optical system and the eye E (first displacement). Further, the deviation compensating optical system is configured to compensate a displacement (second displacement) caused when the eye E is displaced from the optical axis of the ophthalmoscopic optical system. The deviation compensating optical system may be configured to compensate both the first displacement and the second displacement.

As the compensating optical system, for example, a light deflection member to deflect ophthalmoscopic light is used. It is effective that the deviation compensating optical system is configured to allow a lens placed in an optical path of the ophthalmoscopic optical system to move in a vertical direction to the lens optical axis. In this case, for instance, an objective lens is moved. Furthermore, the deviation compensating optical system may be configured to place a light reflection member movably in the optical path of the ophthalmoscopic optical system.

For instance, the compensating optical system is placed in a common optical path of a light projecting system and a light receiving system of the ophthalmoscopic optical system or placed in each of the light projecting system and the light receiving system of the ophthalmoscopic optical system. In a case where an imaging optical system is provided to capture a front image of an examinee's eye through an imaging element, effectively, this optical system is placed in a common optical path of the ophthalmoscopic optical system and the imaging optical system, for example.

The compensating optical system may be configured to be placed in an optical path of one of the light projecting system and the light receiving system of the ophthalmoscopic optical system. In the case of the keratometer, for example, the compensating optical system may be placed only in the light receiving system (e.g., an anterior segment observation system) configured to receive light of an index image. In a configuration capable of measuring both eye refractive power and corneal shape, the compensating optical system may be placed in one of an eye refractive power measuring optical system and a corneal shape measuring optical system.

The aforementioned drive part is provided to drive the compensating optical system based on output from the aforementioned detector. The drive part is for example an actuator capable of moving a lens in a vertical direction relative to an optical axis of the lens and an actuator capable of rotating a mirror. Further, a controller (e.g., a CPU, a control circuit) provided in the main unit controls the drive part based on output from the detector.

In a case where the drive part is provided in the eye refractive power measuring device, effectively, this drive part is configured to drive the compensating optical system so as to bring a region to be measured by the eye refractive power measuring optical system onto a pupil of the eye E.

Further effectively, a computing unit is provided to compensate an eye examination result obtained by the ophthalmoscopic optical system according to the position of the optical member provided in the deviation compensating optical system. For instance, the computing unit provided in the device compensates a measurement result of eye optical characteristics of the eye E according to the position of the lens provided in the compensating optical system.

According to the ophthalmological device in the present embodiment can provide high operability and perform stable measurement/examination. In the case of the eye characteristic measuring device to measure eye optical characteristics, for example, difficulty in positional alignment due to hand shake can be solved during measurement by the eye characteristic measuring device.

In the case of the eye photographing device, when a displacement between the imaging optical axis and the eye E is detected, the compensating optical system is driven based on a detection signal. In the case of a device for imaging a fundus, for example, a control part 80 may be configured to detect a deviation of a fundus image captured by the imaging element for fundus imaging (e.g., for alignment) provided in a fundus observation optical system, and then feedback drive the compensating optical system to compensate the deviation. Of course, an accelerator sensor or the like may be provided.

The present embodiment is applicable to not only the handheld ophthalmological device but also a floor-standing ophthalmological device in case it is installed in an unstable place.

In the present embodiment, furthermore, a light deflection member (e.g., a prism) is provided in a position off a pupil conjugation position and this member is eccentrically rotated about the optical axis, thereby appropriately avoiding disturbance light from entering in an ophthalmoscopic light receiving element.

EXAMPLES

First Example

A first example of the present embodiment will be explained below. The first example of the invention is explained referring to the accompanying drawings. FIG. 1 is an external side view showing one example of a hand-held ophthalmological device of the first embodiment. The following explanation exemplifies an eye refractive power measuring device (an auto-refractometer). In the following explanation, a positional relationship between an examinee's eye and the device is defined assuming that a back and forth direction is a Z direction, a right and left direction is an X direction, and an up and down direction is a Y direction while the examinee's eye and the device face each other.

A main unit 100 is provided with an optical unit 1 including an ophthalmoscopic optical system 10 to project an ophthalmoscopic light beam to the examinee's eye E and receiving reflection light therefrom, a deviation detection unit 60 to detect a deviation (e.g., hand shake of an examiner) applied to the main unit 100, and a deviation compensating unit 70 to compensate a deviation of the ophthalmoscopic light caused by the deviation applied to the main unit 100. A test window 102 is positioned in a side of the main unit 100 that will face the eye E. An operation part 84 and a monitor 85 are positioned in a side of the main unit 100 that will face an examiner. Furthermore, the main unit 100 contains an electric system for control and arithmetic processing. The examiner faces the examinee and holds the main unit 100. While looking at the monitor 85, the examiner makes alignment of the main unit 100 with respect to the eye E.

The deviation compensating unit 70 is provided with a reflection mirror 72 serving as a deviation compensating optical system, and a drive part 74 (e.g., a voice coil motor mechanism) to rotate the reflection mirror 72 in the X and Y directions. The reflection mirror 72 is placed in one of the optical paths of the ophthalmoscopic optical system 10 and is used as a part of the ophthalmoscopic optical system 10. As an alternative, a plurality of reflection mirrors for deviation compensation may be provided (e.g., utilizing a galvano motor mechanism). In this case, one is rotated in the X direction and the other is rotated in the Y direction.

In FIG. 1, the reflection mirror 72 is placed in a position facing the eye E and the ophthalmoscopic optical system 10 is placed below the reflection mirror 72. An optical axis L1 of the ophthalmoscopic optical system 10 is deflected toward the eye E by the reflection mirror 72. The reflection mirror 72 reflects light emitted from the ophthalmoscopic optical system 10 toward the eye E and reflects reflection light from the eye E into the ophthalmoscopic optical system 10.

The reflection mirror 72 is rotated about an intersection point K between the optical axis L1 and the reflection mirror 72. A reference position of the reflection mirror 72 is a position in which the optical axis L1 is parallel to the Z direction. As the reflection mirror 72 is rotated, the optical axis L1 pivots about a predetermined point O on the optical axis L1 (see FIGS. 5(a) to 5(c)). The predetermined point O is brought into coincide with a pupil center Pc by alignment.

The detecting unit 60 includes at least one of an angular velocity sensor and an accelerator sensor to detect a deviated state of the main unit 100. The detecting unit 60 is connected to the drive part 74 which is connected to the reflection mirror 72. With such configuration, the deviation detecting unit 60 detects a deviation amount and the drive part 74 drives the reflection mirror 72 based on output of the deviation detecting unit 60.

In FIG. 1, the detecting unit 60 includes an accelerator sensor 62. This sensor 62 outputs an accelerator signal according to a parallel deviation (shift deviation) of the main unit 100 in the X and Y directions. In addition to the X-Y two-axis sensor, a sensor configured to detect a parallel deviation in the Z direction may also be provided. As an alternative, a single-axis sensor may be provided alone. As the accelerator sensor 62, there are utilizable mechanical, optical, and semiconductor-type (capacitance type, piezoresistance type, gas temperature distribution type) accelerator sensors. The reason why the accelerator sensor 62 is used is that a distance between the main unit 100 and the eye E in the eye examination and measurement is relatively short and thus the parallel deviation is liable to be caused by the examiner. In addition to the accelerator sensor 62, an angular velocity sensor may be provided. In this case, an angular velocity signal according to a rotation deviation of the main unit 100 is output.

FIG. 2 is an optical arrangement diagram showing optical systems contained in the main unit 100 seen from front in the first embodiment. The optical unit 1 is provided with the ophthalmoscopic optical system 10, a light projecting optical system 30 to project a fixation target to the eye E, and an observation optical system 50 to allow observation of the eye E.

In FIG. 2, the ophthalmoscopic optical system 10 is an optical system to objectively measure eye refractive power. The ophthalmoscopic optical system 10 projects a measurement index to a fundus Ef and receives reflection light from the fundus. Based on the light receiving signal, the refractive power of the eye E is measured.

More concretely, the ophthalmoscopic optical system 10 consists of a light projecting optical system 10a to project a spot index onto the fundus Ef through a pupil center Pc and a light receiving optical system 10b to extract fundus reflection light as a ring image through the periphery of a pupil and form a ring-shaped reflection image on an imaging element 26.

The light projecting optical system 10a includes a light source 11, a relay lens 12, a hole mirror 13, an objective lens 14, and the reflection mirror 72, which are arranged on the optical axis L1. The light source 11 is placed in a nearly conjugated position with the fundus Ef and an aperture of the hole mirror 13 is placed in a nearly conjugated position with the pupil of the eye E.

Measurement light emitted from the light source 11 is reflected by the reflection mirror 72 via the relay lens 12, the hole mirror 13, a dichroic mirror 35, a dichroic mirror 53, and the objective lens 14. The measurement light reflected by the reflection mirror 72 passes through the pupil center Pc, projecting a spot-shaped beam onto the fundus Ef.

The light receiving optical system 10b includes the reflection mirror 72, the objective lens 14, the hole mirror 13, a collimator lens 22, a ring lens 24, and the imaging element (e.g., a two-dimensional imaging element such as a CCD and a CMOS) 26. The imaging element 26 is placed in a nearly conjugated position with the fundus Ef via the lens 14, the lens 22, and the ring lens 24. The ring lens 24 consists of a lens part formed with an annular, cylindrical lens and a light shielding part having a ring aperture equal in size to the lens part, and is placed in a nearly conjugated position with the pupil of the eye E. An output signal from the imaging element 26 is connected to the control part 80.

The fundus reflection light by the light projecting optical system 10a is reflected again by the reflection mirror 72, and reflected again by a reflection plane of the hole mirror 13 via the objective lens 14, the dichroic mirror 53, and the dichroic mirror 35, and then is collimated into a nearly parallel beam (in a case of an emmetropic eye) by the collimator lens 22. The ring-shaped beam is extracted by the ring lens 24 and received as a ring image by the imaging element 26.

Instead of the above configurations, various methods may be adopted; e.g., a method of projecting a ring index onto the fundus Ef through the peripheral part of a pupil and extracting reflection light through the pupil center so shat a ring image is received by the imaging element, a phase difference method performed by projecting slit light onto a fundus, and others.

Between the objective lens 14 and the hole mirror 13, the dichroic mirror 35 serving as a beam splitter that reflects visible light and transmits infrared light is placed to deliver the light from the light source 31 toward the eye E. Between the dichroic mirror 35 and the objective lens 14, the dichroic mirror 53 serving as a beam splitter is placed to deliver the light from an anterior segment to the observation optical system 50. The mirror 53 has wavelength characteristics that transmit measurement light and reflect observation light. By those beam splitters, the measurement optical axis, the fixation optical axis, and the observation optical axis are made coaxial with the same optical axis (L1).

The target projecting optical system 30 includes a light source 31 that emits visible light, a fixation target 32 on which a scenic/animal image or others is painted, a light projecting lens 33, a total reflection mirror 34, the dichroic mirror 35, the objective lens 14, and the reflection mirror 72. In addition to the above configuration, as a fixation target, a point light source such as LED and a display such as a liquid crystal display, and others are used. Furthermore, a plurality of fixation targets may be placed two-dimensionally.

The fixation target 32 illuminated by the light source 31 is projected onto the fundus Ef via the light projecting lens 33, the total reflection mirror 34, the dichroic mirror 35, the dichroic mirror 53, the objective lens 14, and the reflection mirror 72. Accordingly, the eye E is induced to hold fixation. The light source 31 and the fixation target 32 are moved in the optical axis direction to apply a fogging to the eye E.

On the outside of the test window 102, first projection optical systems 45 to project ring-shaped finite index images onto the cornea Ec are arranged concentrically with the optical axis L1. Furthermore, second projection optical systems 46 to project infinite index images onto the cornea Ec are arranged left-right symmetric (up-down symmetric for convenience in the figure) with respect to the optical axis L1. The first projection optical systems 45 illuminate the anterior segment with infrared light and are also utilizable as index for measurement of corneal shape (kerato index).

The observation optical system 50 includes the reflection mirror 72, the objective lens 14, the dichroic mirror 53, an imaging lens 51, and a two-dimensional imaging element 52. An output signal from the imaging element 52 is connected to the control part 80 and output to the monitor 85. The observation optical system 50 is used for observation of a front image of the eye E and also used as a detecting optical system for detecting an alignment state of the main unit 100 with respect to the eye E.

An anterior segment image of the eye E illuminated by the first projection optical systems 45 is received by an imaging plane of the imaging element 52 via the reflection mirror 72, the objective lens 14, the dichroic mirror 53, and the imaging lens 51. Similarly, the alignment index images formed by the first projection optical systems 45 and the second projection optical systems 46 are detected by the imaging element 52.

FIG. 3 is a block diagram showing electric and control systems contained in the main unit 100 in the first example. The control part 80 performs control of the whole device and arithmetic processing such as calculation of eye refractive values. The control part 80 is connected to the light source 11, the imaging element 26, the light source 31, the imaging element 52, the operation part 84 to be used for various settings, the monitor 85, the deviation detecting unit 60, the deviation compensating unit 70, a memory 81, and others. For activation of the detecting unit 60 and the compensating unit 70 by the control part 80, a dedicated drive circuit (e.g., an LSI) may be used for speedup. Of course, they may be activated by software.

The control part 80 controls the monitor 85 to display an anterior segment image, a measurement result, and others on a screen in superimposing manner. The control part 80 further detects misalignment (alignment displacement) based on an imaging signal from the imaging element 52.

FIG. 4 shows a ring image captured by the imaging element 26 during measurement. An output signal from the imaging element 26 is stored as image data (measurement image) in the memory 81. Thereafter, the control part 80 detects an image position in each meridian direction based on the image stored in the memory 81, and then performs elliptic approximation using a least square method and others. The control part 80 then determines a refraction error in each meridian direction from the approximated elliptic shape and, based on this determined error, measures eye refraction values; S (Spherical power), C (Cylinder power), and A (Astigmatic axial angle), and displays these values on the monitor 85.

Operations of the device configured as above will be explained. An examiner holds the main unit 100 and instructs an examinee to look at the fixation target 32, and then puts the test window 102 in front of the eye E. Accordingly, an anterior segment is imaged by the imaging element 52. The monitor 85 displays an anterior segment image F, a ring image (Meyer ring image) R formed by the first projection optical systems 45, and infinite index images M projected by the second projection optical systems 46 (see FIG. 3).

The control part 80 detects the alignment state with respect to the examinee's eye based on an imaging signal from the imaging element 52. In this case, the control part 80 determines misalignment in the X and Y directions by calculating a center position (a nearly corneal center) of the ring index R. In case the main unit 100 is displaced in the Z direction, the control part 80 determines misalignment in the Z direction by utilizing characteristics that the interval between the indexes M hardly changes but an image interval of the ring index R changes (for the details, refer to JP-A-6(1994)-46999). The control part 80 increases and decreases the number of indicators G based on an alignment detection result in the Z direction.

Herein, the examiner moves the main unit 100 in the X and Y directions so that the ring image R and a reticle mark LT become concentric. While referring to the indicators G changing based on the alignment detection result in the Z direction (or to adjust the ring image R so as to be thinnest), the examiner moves the main unit 100 in the Z direction.

In the case where auto-shot is thereafter activated, when the alignment state in the X, Y, and Z directions meets a permissible range, the control part 80 generates a trigger signal to start measurement. On the other hand, in the case where auto-shot is turned off, measurement is started upon pressure of a trigger switch provided in the operation part 84.

When a trigger signal is output, the control part 80 turns on the light source 11 to project measurement index onto the fundus Ef. The control part 80 receives the reflection light through the imaging element 26 and detects the index image.

At that time, preliminary measurement is first conducted. Based on a result of this preliminary measurement, the light source 31 and the fixation target plate 32 are moved in the optical axis direction to apply a fogging to the eye E. Thereafter, main measurement on the eye E is performed. In this main measurement, images of a plurality of frames are captured and stored in the memory 81 for addition/accumulation processing of ring images, or multiple measurements.

In the above measurement, the control part 80 supplies power to the sensor 62 and generates a positional displacement signal based on an acceleration signal output from the sensor 62. Upon input of the generated positional displacement signal, the control part 80 further outputs a deviation compensating signal to rotate the reflection mirror 72 in a direction to cancel the shift deviation of the main unit 100.

FIGS. 5(*a*) to 5(*c*) show concrete examples to compensate hand shake during measurement in the first example; FIG. 5(*a*) shows a state before hand shake occurs, FIG. 5(*b*) shows a state immediately after shift displacement occurs due to hand shake, and FIG. 5(*c*) shows a state after the shift displacement is compensated. The control part 80 drives the deviation compensating unit 70 to bring a measurement region of the eye refractive power measuring optical system onto a pupil.

To compensate the hand shake, the optical axis L1 is moved in an opposite direction to movement of the main unit 100 to cancel the displacement of the optical axis L1 with respect to the center of the eye E (e.g., a pupil center Pc, or a corneal center) caused by the hand shake. It is to be noted that the displacement of the optical axis L1 does not need to be cancelled completely as long as it is reduced.

For instance, when the main unit 100 is displaced downward by $\Delta Y$ with respect to a visual line of the eye E due to hand shake of the examiner, a downward deviation amount $\Delta Y$ is generated as a positional displacement signal. The control part 80 then drives the drive part 74 to rotate the reflection mirror 72 upward by $\Delta \theta$ to make the optical axis L1 swing about the pupil center Pc as a swing point.

Measurement light from the light projecting optical system 10*a* is compensated (deflected) by movement of the reflection mirror 72 and then projected onto the fundus Ef via the pupil center Pc. Reflection light from the fundus is reflected by the reflection mirror 72 and made coaxial with the optical axis of the objective lens 14 and then directed toward the imaging element 26. A measurement region by the ophthalmoscopic optical system 10 tracks a pupil of the eye E.

Fixation light of the target projecting optical system 30 is similarly compensated (deflected) by movement of the reflection mirror 72, thereby inducing the eye E to make the visual line thereof coaxial with the optical axis L1. Specifically, the fixation direction of the eye E tracks the optical axis L1. Depending on a reaction speed of the eye E, the fixation direction may remain in a front direction. In the case where the target projecting optical system 30 is placed independent from the reflection mirror 72, the eye E is fixed in the front direction.

Reflection light from the anterior segment is reflected by the reflection mirror 72, and made coaxial with the optical axis of the objective lens 14, and directed toward the imaging element 52. An observation region by the observation optical system 50 tracks the anterior segment of the eye E.

Accordingly, even when the main unit 100 is moved due to hand shake of the examiner, measurement of refractive power, induction of fixation, and observation of anterior segment are enabled. In this case, it is particularly effective in projecting and receiving measurement light successively (e.g., obtaining measurement images of a plurality of frames) to measure refractive power. The above explanation is given to an example only on the control in the Y direction. When the same control is applied to the X direction, furthermore, a positional displacement deriving from hand shake can be compensated in the X and Y directions.

Since the displaced state of the optical axis L1 from the reference position of the eye E (e.g., a corneal apex, or a pupil center) is detected and the compensating optical system is driven accordingly, even the hand-held ophthalmological device difficult to make alignment can perform stable measurement/examination.

As shown in FIG. 2, the deviation compensating optical system (72) is placed in an common optical path of the light projecting system and the light receiving system of the ophthalmoscopic optical system 10, so that an incoming position and an outgoing position of light with respect to the eye are appropriately compensated, allowing accurate measurement (examination) to be performed. The deviation compensating optical system may also be placed in each of the light projecting system and the light receiving system.

As shown in FIG. 2, since the deviation compensating optical system is placed in the common optical path of the ophthalmoscopic optical system 10 and the observation optical system 50, the deviation of the observation image is also compensated. This enables stable observation and measurement (examination).

In the above explanation, an optical reflection member (e.g., a reflection mirror, a reflection prism) is used as a compensating optical member to deflect ophthalmoscopic light to make displacement compensation. Accordingly, the light incident on the compensating optical member is caused to travel toward the eye E. Thus, disturbed light is avoided from entering the ophthalmoscopic light receiving element during movement of the optical member.

In this case, when a light deflection member (e.g., a prism) is provided in a position off the pupil conjugation position and this member is eccentrically rotated about the optical axis L1, the disturbed light is further appropriately removed.

Of course, even another compensating optical member may achieve fixed effects. In this case, it is preferably arranged such that, when the main unit 100 and the eye E are displaced in position, the optical member is moved to maintain a conjugated relationship between the pupil of the eye E and the ring lens 24 in the X and Y directions. For example, the objective lens 14 placed in the common optical path of the light projecting optical path and the light receiving optical path may be moved vertically with respect to the optical axis. Of course, an optical member (e.g., a concave lens) special for optical axis displacement may be placed. As another alternative, a plurality of optical members may be provided.

Furthermore, the ring lens 24 and the imaging element 26 may be moved in a vertical direction with respect to the optical axis of the lens 22 (the light source 11 may be moved in sync therewith). The imaging element 26 may be used as a deviation detecting system. For instance, based on an imaging signal from the imaging element 26, the compensating optical system is moved to make the center of a ring image on the imaging element 26 coincide with the optical axis.

The above explanation uses the sensor (the detecting unit 60) configured to detect the movement of the main unit 100. As an alternative, the imaging element configured to image the eye E may be used as a deviation detecting sensor. For instance, the control part 80 detects a deviation from an imaging result of the imaging element 52, and feedback drives the compensating optical system so that the corneal center (or a pupil center) falls within a permissible range from a certain alignment reference position (e.g., an intersection point between the imaging plane and the optical axis L1). According to the present technique, even when the eye E moves with respect to the main unit 100 in the driving range of the compensating optical system, the position displacement is compensated.

In the above explanation, hand shake detection and compensating operation may be started at the time when the misalignment falls within a certain permissible range (e.g., wider than an alignment completion range). As an alternative, the hand shake compensating operation may be started in response to an output signal from the operation part 84.

When the misalignment is to be detected from output from the imaging element 52, a deviation amount detected by the detecting unit 60 with respect to an actual displacement amount may be offset (compensated). At the time of compensating the hand shake, alignment detection and result output may be stopped.

The above explanation exemplifies the auto-refractometer. However, the present invention is also applicable to any other ophthalmological devices. For instance, the invention is also applicable to a hand-held type fundus photographing device (e.g., a fundus camera, an ophthalmic OCT). In this case, the displacement between the imaging optical axis and the eye E due to hand shake is detected and the compensating optical system is driven based on a detection signal thereof.

In the case of the device of imaging a fundus, for example, a control part may detect a deviation of a fundus image captured by an imaging element for fundus imaging (e.g., for alignment) provided in a fundus observation optical system and feedback drive a compensating optical system to compensate the deviation. Of course, an accelerator sensor and others may also be provided.

The present invention is applicable to not only the hand-held ophthalmological device but also a floor-standing ophthalmological device in case it is installed in an unstable place.

In the above explanation, the hand-held ophthalmological device configured to project measurement light onto a fundus and receive reflection light therefrom to measure eye characteristics (e.g., eye refractive power, ocular axial length) uses the sensor configured to detect a deviation applied to the main unit 100. However, the invention is not limited thereto.

For instance, a light deflection member (e.g., a prism, a mirror, etc.) may be provided in an optical path of a measuring optical system and driven to change a passage region of the measurement light on an anterior segment as needed to measure a deviation. The light deflection member is placed for example in a position off a conjugated position of the measuring optical system with a pupil. To be specific, a prism is eccentrically rotated about the optical axis L1 to eccentrically rotate the passage region. Further, the mirror is reciprocated up and down to move the passage region up and down.

With the above manner, the passage region of the measurement light is rapidly moved with respect to the anterior segment, thereby cancelling out the displacement of the measurement light due to hand shake. Accordingly, the measurement is easily performed by receiving the measurement light at the time of cancelling.

Second Example

A second example of the present embodiment will be explained below. FIG. 6 is an external side view showing one example of a hand-held ophthalmological device of the second example. The following explanation exemplifies an eye refractive power measuring device (an auto-refractometer). In the following explanation, a positional relationship between an examinee's eye and the device is defined assuming that a back and forth direction is a Z direction, a right and left direction is an X direction, and an up and down direction is a Y direction while the examinee's eye and the device face each other.

The main unit 100 is provided with the optical unit 1 and a compensating unit 110. The optical unit 1 includes the ophthalmoscopic optical system 10 to project an ophthalmoscopic light beam onto the examinee's eye and receive reflection light therefrom. The test window 102 is positioned in the side of the main unit 100 that will face the eye E. The operation part 84 and the monitor 85 are positioned in the side of the main unit 100 that will face an examiner. Furthermore, the main unit 100 contains an electric system for control and arithmetic processing. The examiner faces the examinee and holds the main unit 100. While looking at the monitor 85, the examiner makes alignment of the main unit 100 with respect to the eye E.

The compensating unit 110 is provided to compensate a relative positional displacement between the ophthalmoscopic optical axis L1 of the ophthalmoscopic optical system 10 and the eye E. The compensating unit 110 is provided with for example the objective lens 14 and a drive part 111, which serve as the compensating optical system. The objective lens 14 is placed movably on a plane vertical to the optical axis of the objective lens 14. The drive part 111 is provided to shift (move) the objective lens 14 in a vertical direction (a direction perpendicular to the measurement optical axis L1) with respect to the optical axis of the objective lens 14. The objective lens 14 is placed in one of the optical paths of the ophthalmoscopic optical system 10 and is used as a part of the ophthalmoscopic optical system 10.

In FIG. 6, the optical axis L1 of the ophthalmoscopic optical system 10 is deflected toward the eye E by the reflection mirror 72. The reference position of the objective lens 14 is a position in which the optical axis L1 formed by a lens system (e.g., a lens 12) other than the objective lens 14 of the ophthalmoscopic optical system 10 and the optical axis of the objective lens 14 become coaxial. In the present example, the optical axis L1 of the ophthalmoscopic optical system 10 is deflected toward the eye E by the reflection mirror 72, but it is not limited to this configuration. For instance, it may be arranged so that the optical axis L1 of the ophthalmoscopic optical system 10 directly goes to the eye E.

When the objective lens 14 is shifted by driving of the drive part 111, the optical axis L1 is deflected, thereby adjusting the optical axis L1 to pass through the pupil center Pc (see FIG. 10).

FIG. 7 is an optical arrangement diagram of the optical systems contained in the main unit 100 seen from front in the second example. The optical unit 1 is provided with the ophthalmoscopic optical system 10, the target projecting optical system 30 to project a fixation target to the eye E, the observation optical system 50 to allow observation of the eye E, and a front projection optical system 120 to form a luminescent spot (a bright spot) at a corneal apex of the eye E.

In FIG. 7, the ophthalmoscopic optical system 10 is an optical system to objectively measure eye refractive power. The ophthalmoscopic optical system 10 projects a measurement index to an examinee's eye and receive reflection light from the examinee's eye acquired by the measurement index. Based on the light receiving signal, the refractive power of the eye E is measured.

To be specific, the ophthalmoscopic optical system 10 consists of a light projecting optical system 10a to project a measurement index (a spot index) onto the fundus Ef through the pupil center Pc and a light receiving optical system 10b to extract fundus reflection light as a ring image through the periphery of a pupil and form (receive) a ring-shaped reflection image on the imaging element 26.

The light projecting optical system 10a includes the light source 11, the relay lens 12, the hole mirror 13, the objective lens 14, and the reflection mirror 72, which are arranged on the optical axis L1. The light source 11 is placed in a nearly conjugated position with the fundus Ef and an aperture of the hole mirror 13 is placed in a nearly conjugated position with the pupil of the eye E.

Measurement light emitted from the light source 11 is reflected by the reflection mirror 72 via the relay lens 12, the hole mirror 13, the dichroic mirror 35, the dichroic mirror 53, and the objective lens 14. The measurement light reflected by the reflection mirror 72 passes through the pupil center Pc, projecting a spot-shaped beam onto the fundus Ef.

The light receiving optical system 10b includes the reflection mirror 72, the objective lens 14, the hole mirror 13, the collimator lens 22, the ring lens 24, and the imaging element (e.g., a two-dimensional imaging element such as a CCD and a CMOS) 26. The imaging element 26 is placed in a nearly conjugated position with the fundus Ef via the objective lens 14, the lens 22, and the ring lens 24. The ring lens 24 consists of a lens part formed with an annular, cylindrical lens and a light shielding part having a ring aperture equal in size to the lens part. The ring lens 24 is placed in a nearly conjugated position with the pupil of the eye E with respect to the objective lens 14. An output signal from the imaging element 26 is connected to the control part 80.

The fundus reflection light, which is formed by projection to the fundus Ef by the light projecting optical system 10a and reflection from the fundus Ef, is reflected again by the reflection mirror 72, and reflected again by the reflection plane of the hole mirror 13 via the objective lens 14, the dichroic mirror 53, the dichroic mirror 35, and then is collimated into a nearly parallel beam (in a case of an emmetropic eye) by the collimator lens 22. The ring-shaped beam is extracted by the ring lens 24 and received as a ring image by the imaging element 26.

Instead of the above configurations, various methods may be adopted; e.g., a method of projecting a ring index onto the fundus Ef through the peripheral part of a pupil and extracting reflection light through the pupil center so that a ring image is received by the imaging element, a phase difference method performed by projecting slit light onto a fundus, and others. Furthermore, a configuration to extract an intermittent ring image, not a continuous ring image, may be adopted. Another configuration to extract a fundus reflection image consisting of point images arranged in a nearly ring form may also be adopted.

The target projecting optical system 30 includes the light source 31 that emits visible light, the fixation target 32 on which a scenic/animal image or others is painted, the light projecting lens 33, a dichroic mirror 125, the dichroic mirror 35, the objective lens 14, and the reflection mirror 72. In addition to the above configuration, as a fixation target, a point light source such as LED and a display such as a liquid crystal display, and others are used. Furthermore, a plurality of fixation targets may be placed two-dimensionally.

The fixation target 32 illuminated by the light source 31 is projected onto the fundus Ef via the light projecting lens 33, the dichroic mirror 125, the dichroic mirror 35, the dichroic mirror 53, the objective lens 14, and the reflection mirror 72. Accordingly, the eye E is induced to hold fixation. The light source 31 and the fixation target 32 are moved in the optical axis direction to apply a fogging to the eye E.

The front projection optical system 120 is provided with a light source 121 that emits near infrared light, a light projecting lens 122, the dichroic mirror 35, the objective lens 14, and the reflection mirror 72. The light source 121 used herein is for example an LED (Light Emitting Diode) light source.

Light emitted from the light source 121 is made into nearly parallel light by the objective lens 14 via the light projecting lens 122, the dichroic mirror 125, the dichroic mirror 35, and the dichroic mirror 53, and then reflected by the reflection mirror 72. Light reflected by the reflection mirror 72 is projected as an infinite index onto a cornea Ec. The front projection optical system 120 projects an index onto the eye E from front, thereby forming a corneal luminescent spot (an index image) at an apex of the cornea Ec. This corneal luminescent spot is used for detection of the relative positional displacement between the ophthalmoscopic optical axis L1 and the eye E (the details will be described later).

Between the light projecting lens 122 and the dichroic mirror 35, the dichroic mirror 125 that reflects visible light and transmits infrared light is placed to deliver the light from the light source 31 toward the eye E. Between the objective lens 14 and the hole mirror 13, the dichroic mirror 35 serving as a beam splitter is placed to deliver the light from the light source 31 and the light source 121 to the eye E. The dichroic mirror 35 has wavelength characteristics that reflect light of the light source 121 and the light source 31 and transmit light of the light source 11. Between the dichroic mirror 35 and the objective lens 14, furthermore, the dichroic mirror 53 serving as a beam splitter is placed to direct the light from an anterior segment to the observation optical system 50. The mirror 53 has wavelength characteristics that transmit measurement light and reflect observation light. By those beam splitters, the measurement optical axis, the fixation optical axis, and the observation optical axis are made coaxial with the same optical axis (L1).

On the outside of the test window 102, the first projection optical systems 45 to project ring-shaped finite index images onto the cornea Ec are arranged concentrically with the optical axis L1. Furthermore, the second projection optical systems 46 to project infinite index images onto the cornea Ec are arranged left-right symmetric (up-down symmetric for convenience in the figure) with respect to the optical axis L1. The first projection optical systems 45 illuminate the anterior segment with infrared light and are also utilizable as index for measurement of corneal shape (kerato index).

The observation optical system 50 includes the reflection mirror 72, the objective lens 14, the dichroic mirror 53, the imaging lens 51, and the two-dimensional imaging element 52. An output signal from the imaging element 52 is connected to the control part 80 and output to the monitor 85. The observation optical system 50 is used for observation of a front image of the eye E and also used as a detecting optical system for detecting an alignment state of the main unit 100 with respect to the eye E.

An anterior segment image of the eye E is received by an imaging plane of the imaging element 52 via the reflection mirror 72, the objective lens 14, the dichroic mirror 53, the dichroic mirror 54, and the imaging lens 51. Similarly, the alignment index images formed by the first projection optical systems 45 and the second projection optical systems 46 are detected by the imaging element 52. Between the dichroic mirror 53 and the imaging lens 51, a dichroic mirror 54 serving as a beam splitter is placed to direct the corneal reflection light formed by the light source 121, of the light from the anterior segment, to an XY alignment detecting optical system 150 (hereinafter, simply referred to as a detecting optical system 150). The mirror 54 has wavelength characteristics that transmit light of the first projection optical systems 45 and the second projection optical systems 46 and reflect light of the front projection optical system 120.

The detecting optical system 150 is provided to rapidly detect the relative positional displacement between the ophthalmoscopic optical axis L1 of the ophthalmoscopic optical system 10 and the eye E. The detecting optical system 150 includes the reflection mirror 72, the objective lens 14, the dichroic mirror 53, the dichroic mirror 54, a light receiving lens 55, and an optical position sensor (PSD: Position Sensitive Detector) 56.

For instance, the detecting optical system 150 is used to detect the positional displacement based on a corneal luminescent spot formed by the front projection optical system 120 and detected by the PSD 56. An output signal from the PSD 56 is connected to the control part 80 and output to the monitor 85.

The PSD is a semiconductor position detecting device, which is a photosensor capable of detecting the position of a spot light. An output signal from the PSD is an output signal representing positional data of the corneal luminescent spot itself and thus enables prompt acquisition of positional data of the corneal luminescent spot.

The PSD enables enhanced speed of the processing from light reception to displacement detection as compared with a two-dimensional imaging element such as CCD. Accordingly, since a severe positional displacement due to hand shake or the like is detected by use of the PSD, the displacement can be compensated at high speed.

The corneal center luminescent spot (the index image) projected by the front projection optical system 120 is received by the light receiving plane of the PSD 56 via the reflection mirror 72, the objective lens 14, the dichroic mirror 53, the dichroic mirror 54, and the imaging lens 55.

FIG. 8 is a block diagram showing electric and control systems contained in the main unit 100 in the second example. The control part 80 performs control of the whole device and arithmetic processing such as calculation of eye refractive values. The control part 80 is connected to the light source 11, the imaging element 26, the light source 31, the light source 121, the imaging element 52, the PSD 56, the operation part 84 to be used for various settings, the monitor 85, the compensating unit 110, the memory 81, and others. For activation of the compensating unit 110 by the control part 80, a dedicated drive circuit (e.g., an LSI) may be used for speedup. Of course, they may be activated by software.

The control part 80 controls the monitor 85 to display an anterior segment image, a measurement result, and others on a screen in superimposing manner. The control part 80 further detects a misalignment amount and a hand shake amount based on an imaging signal from the PDS 56. In the present example, misalignment caused by an examinee and hand shake caused by an examiner are detected by the PSD 56. As an alternative, the misalignment detection and the hand shake detection may be performed based on the imaging signal from the imaging element 52.

FIG. 4 shows a ring image captured by the imaging element 26 during measurement. An output signal from the imaging element 26 is stored as image data (measurement image) in the memory 81. Thereafter, the control part 80 detects an image position in each meridian direction based on the image stored in the memory 81, and then performs elliptic approximation using a least square method and others. The control part 80 then determines a refraction error in each meridian direction from the approximated elliptic shape and, based on this determined error, measures eye refraction values; S (Spherical power), C (Cylinder power), and A (Astigmatic axial angle), and displays these values on the monitor 85.

Operations of the device configured as above will be explained. An examiner holds the main unit 100 and instructs an examiner to look at the fixation target 32, and then puts the test window 102 in front of the eye E. Accordingly, an anterior segment is imaged by the imaging element 52. The monitor 85 displays an anterior segment image. FIG. 9 shows one example of a display screen of the monitor 85. On the monitor 85, there are displayed the anterior segment image F, a ring image (Meyer ring image) R formed by the first projection optical systems 45, infinite index images M projected by the second projection optical systems 46, and a corneal center index (an infinite corneal center luminescent spot) C projected by the front projection optical system 120.

The control part 80 detects a relative positional displacement between the eye E and the optical axis L1 based on a light receiving signal from the PSD 56. The relative positional displacement includes at least one of a displacement caused when the main unit 100 is moved with respect to the eye E (e.g., hand shake), a displacement caused when the eye E is moved with respect to the main unit 100 (e.g., involuntary eye movement), and a displacement caused before completion of alignment with respect to the eye E.

For instance, based on the light receiving signal from the PSD 56, the control part 80 detects the relative displacement between the optical axis L1 of the ophthalmoscopic optical system 10 and the examinee's eye in a direction perpendicular to the optical axis L1 of the ophthalmoscopic optical system 10. The control part 80 calculates the corneal center luminescent spot C to determine the positional displacement in the X and Y directions of the optical axis L1 with respect to the eye E. The control part 80 utilizes the characteristics that when the main unit 100 is displaced in the Z direction, the interval between the indexes M hardly changes but the image interval of the ring index R changes (for the details, refer to JP-A-6 (1994)-46999). The control part 80 increases and decreases the number of indicators G based on an alignment detection result in the Z direction.

Herein, the examiner moves (shifts) the main unit 100 in the X and Y directions so that the corneal center luminescent spot C falls within the reticle mark LT. The reticle mark LT in the present example electronically represents the reference position set as a position where the corneal apex position and the optical axis L1 of the device coincide with each other. While referring to the indicators G changing based on the alignment detection result in the Z direction (or to adjust the ring image R so as to be thinnest), the examiner moves the main unit 100 in the Z direction.

In the case where auto-shot is thereafter activated, when the alignment state in the X, Y, and Z directions falls within a permissible range, the control part 80 generates a trigger signal to start measurement. On the other hand, in the case where auto-shot is turned off, measurement is started upon pressure of a trigger switch provided in the operation part 84.

When the trigger signal is output, the control part 80 turns on the light source 11 to project measurement index to the fundus Ef. The control part 80 further turns off the first projection optical systems 45, the second projection optical systems 46, the front projection optical system 120 (the light source 121). Specifically, to prevent overlapping of the measurement light with another light from influencing a measurement result or an image to be observed, the control part 80 turns on the light source 11 at the time when the first projection optical systems 45 to the front projection optical system 120 are turned off. The control part 80 turns off the light source 11 at the time when the first projection optical systems 45 to the front projection optical system 120 are turned on. Thus, the control part 80 receives the reflection light by the imaging element 26 and detects the index image.

At that time, preliminary measurement is first conducted. Based on a result of this preliminary measurement, the light source 31 and the fixation target plate 32 are moved in the optical axis direction to apply a fogging to the eye E. Thereafter, main measurement on the eye E is performed. In this main measurement, images of a plurality of frames are captured and stored in the memory 81 for addition/accumulation processing of ring images, or multiple measurements.

At that time, when measurement is performed more than one time, the control part 80 makes detection of an alignment state and detection of hand shake by the first projection optical systems 45 to the front projection optical system 120 every time one frame image is acquired.

For instance, when the control part 80 starts measurement and then acquires one frame image, the control part 80 turns off the light source 11 and turns on the first projection optical systems 45 to the front projection optical system 120. The control part 80 drives the drive part 111 based on the light receiving signal from the PSD 56 to compensate the positional displacement. After completion of displacement compensation, the control part 80 turns on the light source 11 at the time of turning off the first projection optical systems 45 to the front projection optical system 120 and acquires a next one frame image. During measurement, specifically, the light of the light source 11 and the light of another optical system (e.g., the first projection optical systems 45, the second projection optical systems 46, and the front projection optical system 120) are alternately blinked at high speed to perform measurement. Respective lights of the light source 11, the first projection optical systems 45, the second projection optical systems 46, and the front projection optical system 120 may be fast blinked in turn.

An explanation is given to the hand shake compensation using the front projection optical system. The device in the present example compensates the shift displacement in the X and Y directions of the main unit 100 caused by hand shake.

The control part 80 detects, through the PSD 56, the shift displacement (displacement amount and displacement direction) between the corneal luminescent spot C formed on the cornea Ec and the reticle LT. At that time, a displacement amount until the corneal center luminescent spot C *comes* to enter a predetermined permissible range of the previously set reticle mark LT (the reference position) is detected as shift displacement. The control part 80 drives the drive part 111 based on the detected shift displacement to shift the objective lens 14, thereby compensating the shift displacement caused by the hand shake. Specifically, the control part 80 outputs a displacement compensating signal to shift the objective lens 14 in a direction to cancel out the shift deviation of the main unit 100.

The aforementioned predetermined permissible range is set for example to a range in which a positional displacement can be compensated by driving of the compensating unit 110 (e.g., within a range of 1.0 mm displacement in each direction).

FIGS. 10(*a*) to 10(*c*) show concrete examples to compensate hand shake during measurement in the second example; FIG. 10(*a*) shows a state before hand shake occurs, FIG. 10(*b*) shows immediately after a shift displacement is caused by hand shake, and FIG. 10(*c*) shows a state after the shift displacement is compensated. The control part 80 drives the deviation compensating unit 110 to bring the measurement region formed by the eye refractive power measuring optical system to a position on the pupil.

To compensate the hand shake, the control part 80 controls driving of the drive part 111, and moves the optical axis L1 in an opposite direction to movement of the main unit 100 in order to cancel the displacement of the optical axis L1 with respect to the center of the eye E (e.g., the pupil center Pc or the corneal center) caused by the hand shake. It is to be noted that the displacement of the optical axis L1 does not need to be cancelled completely as long as it is reduced.

For instance, when the main unit 100 is displaced downward by ΔY with respect to a visual line of the eye E due to hand shake of the examiner, a downward displacement ΔY is detected. The control part 80 then drives the drive part 111 to shift (move) the lens 14 by ΔS in a direction indicated by an arrow A to compensate the shift displacement ΔY.

Measurement light from the light projecting optical system 10*a* is compensated (deflected) by movement of the objective lens 14 and then projected onto the fundus Ef via the pupil center Pc. The reflection light from the fundus is compensated by the objective lens and made coaxial with the optical axis of the objective lens 14, and directed toward the imaging element 26. The measurement region by the ophthalmoscopic optical system 10 tracks the corneal apex of the eye E.

Fixation light of the target projecting optical system 30 is similarly compensated (deflected) by movement of the objective lens 14, thereby inducing the eye E to hold fixation on the test window 102, so that the visual line of the eye E becomes coaxial with the optical axis L1. Depending on a reaction speed of the eye E, the fixation direction may remain a front direction. In the case where the target projecting optical system 30 is placed independent from the objective lens 14, the eye E is fixed in the front direction.

When the objective lens 14 is moved from the reference position, the reflection light formed by the first projection optical systems 45 and the second projection optical systems 46 and reflected from the anterior segment is deflected by the objective lens 14, and made coaxial with the optical axis of the lens 51 placed downstream of the objective lens 14. This light is received by the imaging element 52.

When the objective lens 14 is moved from the reference position, the reflection light formed by the front projection optical system 120 and reflected from the anterior segment is deflected by the objective lens 14 to become coaxial with the optical axis of the lens 55 disposed downstream of the objective lens 14. This light is received by the PSD 56.

The above configuration enables measurement of eye refractive power, induction of fixation, and observation of anterior segment even when the main unit 100 is relatively moved due to hand shake of the examiner or movement of the examinee. In this case, it is particularly effective in continuously projecting and receiving measurement light (e.g., obtaining measurement images of a plurality of frames) to measure refractive power. The above explanation is given to an example only on the control in the Y direction. When the same control is applied to the X direction, furthermore, the positional displacement deriving from hand shake can be compensated in the X and Y directions.

Since the displacement of the optical axis L1 from the eye E is detected and the compensating optical system is driven accordingly, even the hand-held ophthalmological device difficult to make alignment can perform stable measurement/examination.

The above compensation is also effective in compensating a displacement caused when the eye E moves with respect to the main unit 100 (e.g., involuntary eye movement) and a displacement caused before completion of alignment with respect to the eye E.

In the case of the hand-held ophthalmological device, including no alignment movement mechanism (e.g., a motor mechanism to move the main unit in three dimensional directions, and others) of the floor-standing ophthalmological device, it is difficult to move the main unit to an alignment completion position. When continuous measurement is performed after completion of alignment, the eye moves by involuntary eye movement and thus re-adjustment is needed. Since it is normally necessary to measure both eyes and make alignment for each eye, alignment adjustment takes time.

According to the above configuration, the examiner has only to move the main unit 100 to a range where the positional displacement can be compensated by driving of the compensating unit 110. This largely improves an alignment operation of the hand-held ophthalmological device.

As shown in FIG. 7, the deviation compensating unit 110 is placed in a common optical path of the light projecting system and the light receiving system of the ophthalmoscopic optical system 10, so that an incoming position and an outgoing position of light with respect to the eye are appropriately compensated, allowing accurate measurement (examination) to be performed. The deviation compensating optical system may also be placed in each of the light projecting system and the light receiving system.

As shown in FIG. 7, the deviation compensating optical system is placed in the common optical path of the ophthalmoscopic optical system 10 and the observation optical system 50, a deviation of the observation image is also compensated. This enables stable observation and measurement (examination).

In the present example, the hand shake compensation in the Z direction may be further performed. This hand shake compensation in the Z direction may be conducted by a configuration to adjust focus using an optical member or by compensating a measurement result from the displacement amount in the Z direction. When the measurement result is to be compensated from the displacement amount in the Z direction, for example, the measurement result is compensated by use of a measurement result compensating table of compensation amounts set according to displacement amounts in the Z direction. The measurement result compensating table may be created in advance by calculating compensation values of measurement results according to displacement amounts in the Z direction, and stored in the memory 81.

Of course, even another compensating optical member can provide fixed effects. For instance, a light reflection member (e.g., a reflection mirror or a reflection prism) may be used as a compensating optical system to deflect ophthalmoscopic light in order to compensate the displacement. Of course, a special optical member (e.g., a concave lens) for optical axis displacement may be disposed. A plurality of optical members may be adopted.

In the present example, if the corneal center luminescent spot is not detected, the misalignment may be compensated to a position where the corneal center luminescent spot is detectable by use of the ring image R projected by the first projection optical systems. An alternative is to detect misalignment in the X and Y directions by the ring image R projected by the first projection optical systems and detect a shift displacement due to hand shake by the corneal center luminescent spot.

If the displacement amount between the optical axis L1 and the eye E exceeds a certain permissible range (e.g., a range that is wider than an alignment completion range and allows compensation by lens movement), the control part 80 may cause the monitor 85 to display an indication to prompt movement of the main unit 100. For instance, an arrow or other indication for helping alignment may be displayed on the monitor 85. In this case, the control part 80 may stop compensation control using the lens.

In the present example, the control part 80 may detect a rough positional displacement between the eye E and the optical axis L1 based on an imaging signal from the imaging element 52, and detect a fine positional displacement between the eye E and the optical axis L1 based on the light receiving signal from the PSD 56.

In the present example, the hand shake detection and the compensating operation may be started at the time when the misalignment falls within a certain permissible range (e.g., wider than the alignment completion range). As another alternative, the output signal from the operating part 84 may trigger the hand shake compensating operation. When the objective lens 14 reaches a limit of a movable range, the control part 80 stops driving of the deviation compensating unit 110, returns the objective lens 14 to the reference position, and restarts the compensating operation. In this case, for example, the state where the test window 102 is placed in front of the eye E is detected based on the output signal from the PSD 56, and the compensation is stared.

In the present example, the configuration to detect the positional displacement is configured to optically detect a relative positional displacement between the optical axis L1 of the ophthalmoscopic optical system 10 and the anterior segment of the examinee's eye by use of the detecting optical system 120 (PSD 56). However, the present invention is not limited thereto. It may be arranged to detect the relative positional displacement by utilizing both the detection result of the accelerator sensor and the detection result of the PSD to thereby compensate the positional displacement. For instance, the device in the second example is additionally provided with an accelerator sensor. The control part 80 controls the drive mechanism 111 based on a detection signal from the accelerator sensor to compensate the hand shake and controls the drive mechanism 111 based on a light receiving signal from the PSD to compensate the positional displacement caused when the eye moves.

In the present example, the control part 80 may compensate the measurement result of eye optical characteristics of the examinee's eye according to at least the position of the lens.

For instance, the measurement results may be compensated based on the misalignment amount in the X and Y directions, the focus displacement amount (displacement amount in the Z direction), and the position of the objective lens 14 for displacement compensation. This is because the measurement result may vary if the objective lens 14 is deviated with respect to another optical member of the ophthalmoscopic optical system 10. In the hand-held ophthalmic measuring device (auto-refractometer (keratometer)), preferably, an anterior segment image, a pupil image, and others are stored together with the measurement result in the memory 81 during measurement. A positional relationship between the device and the eye E is detected based on such an image and is used for compensation of the measurement result (for example, astigmatic axial angle). In a case of performing the examination on a bedridden examinee who takes uneasy posture, for example, the control part 80 detects a tilted state between the device and the eye E by using an image stored in the memory 81, and compensates the measurement result based on the tilted state.

In compensating the measurement result, for example, the measurement result compensating table is used for compensation of the measurement result. For the measurement result compensating table, compensating amounts according to positions of the objective lens 14 on a plane vertical to the optical axis of the objective lens 14 are determined in advance by experiments or simulation. Each compensating value of the measurement result corresponding to each position is calculated in advance to create the table.

In the present embodiment, when the light source 11 is turned on, the first projection optical systems 45, the second projection optical systems 46, and the front projection optical system 120 are turned off. The invention is not limited thereto. For instance, the first projection optical systems and the second projection optical systems may be held turned-on even during turn-on of the light source 11. In this case, it is more preferable to use light sources different in wavelength to prevent interference of light between the light sources.

REFERENCE SIGNS LIST

Figure 1:
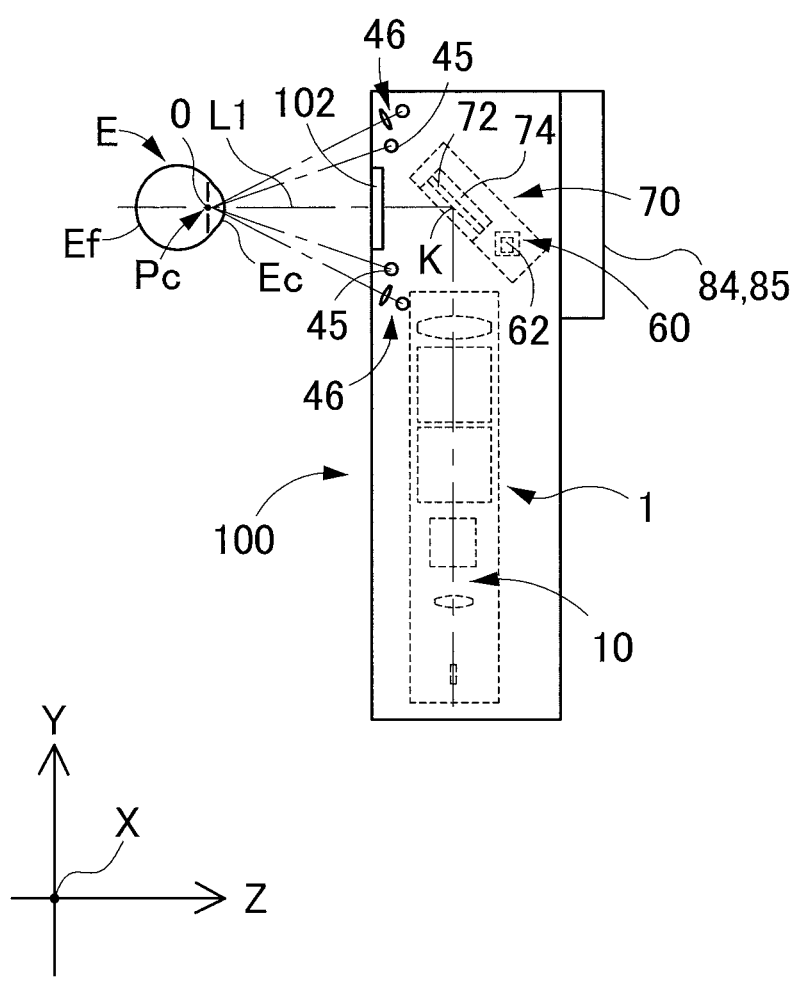
FIG. 1 is an external side view showing one example of a hand-held ophthalmological device in a first embodiment.
Figure 2:
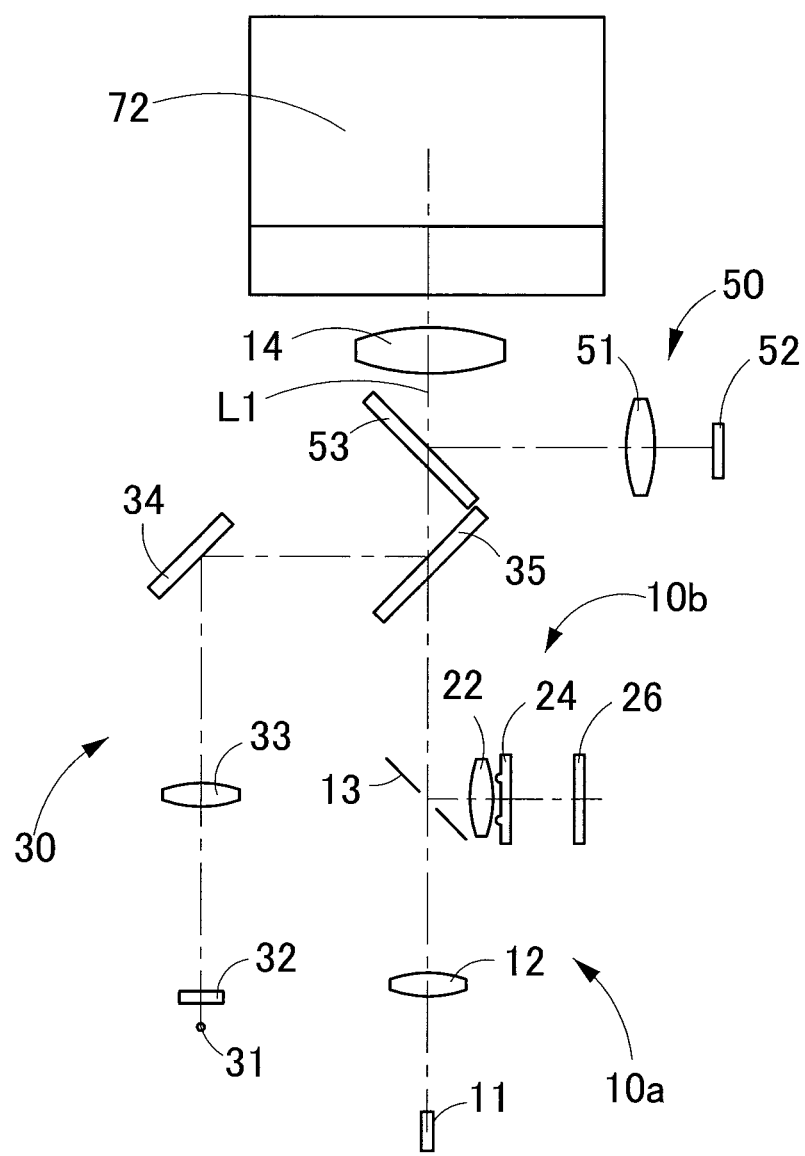
FIG. 2 is an optical arrangement diagram of optical systems contained in a main unit seen from front in a first example.
Figure 3:
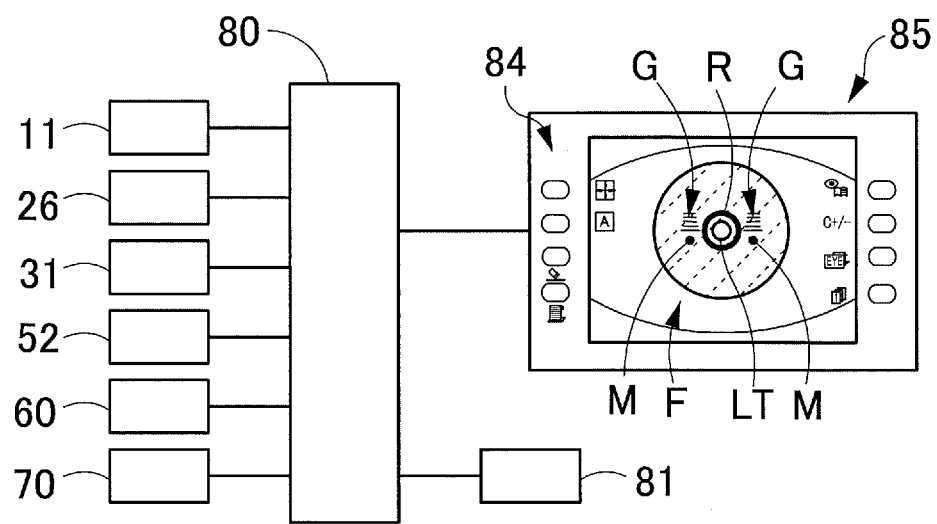
FIG. 3 is a block diagram showing electric and control systems contained in the main unit of the first example.
Figure 4:
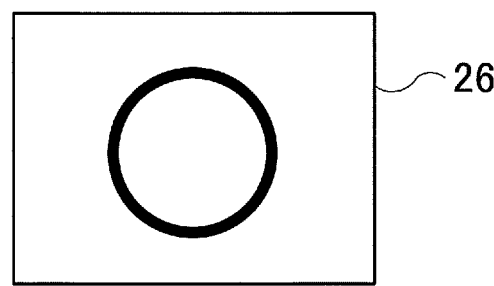
FIG. 4 is a ring image captured by an imaging element during measurement.
Figure 5:
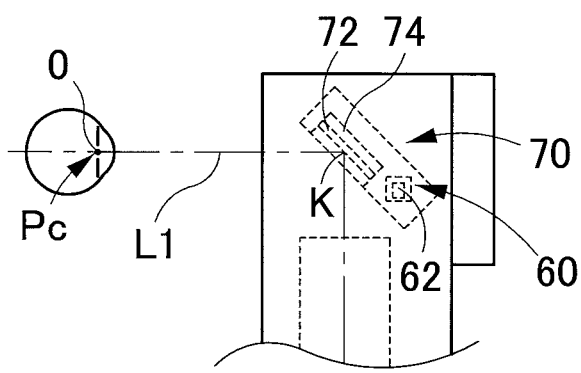
FIGS. 5(*a*) to 5(*c*) show concrete examples to compensate hand shake during measurement in the first example.
Figure 5:
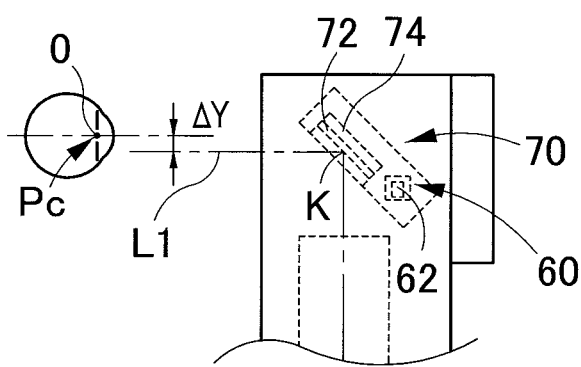
Figure 5:
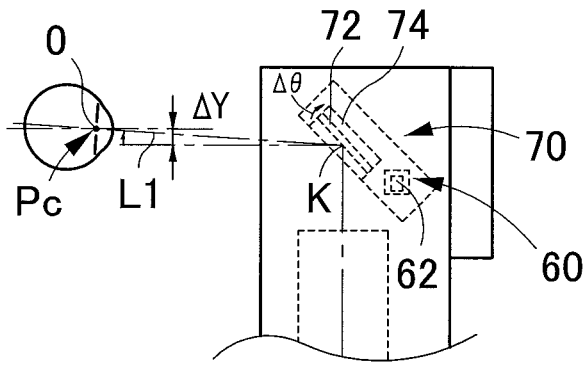
Figure 6:
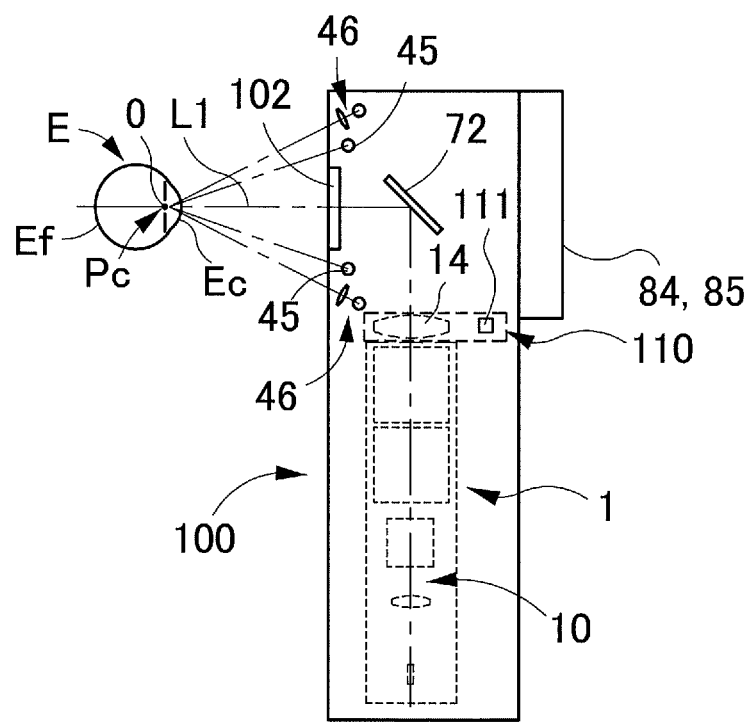
FIG. 6 is an external side view showing one example of a hand-held ophthalmological device of a second example.
Figure 7:
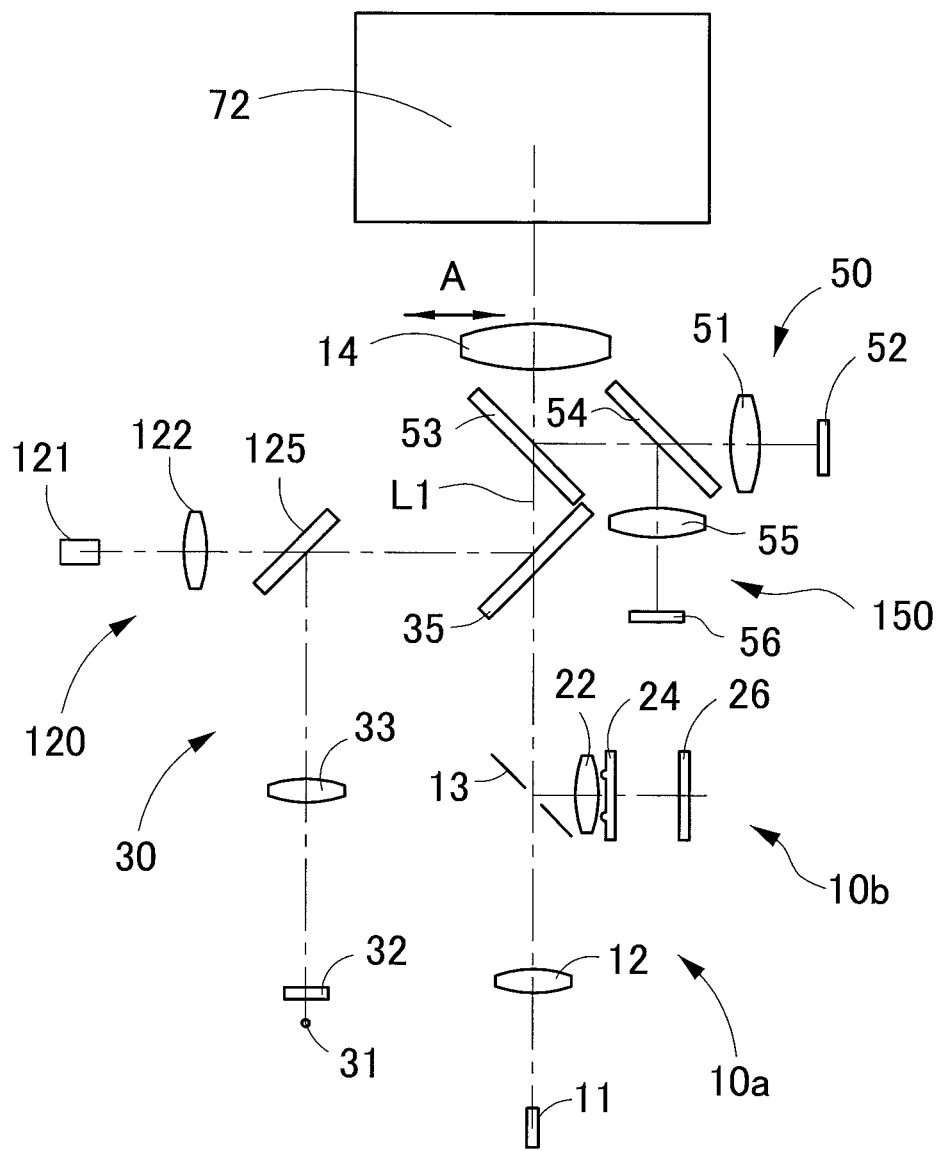
FIG. 7 is an optical arrangement diagram of optical systems contained in a main unit seen from front in the second example.
Figure 8:
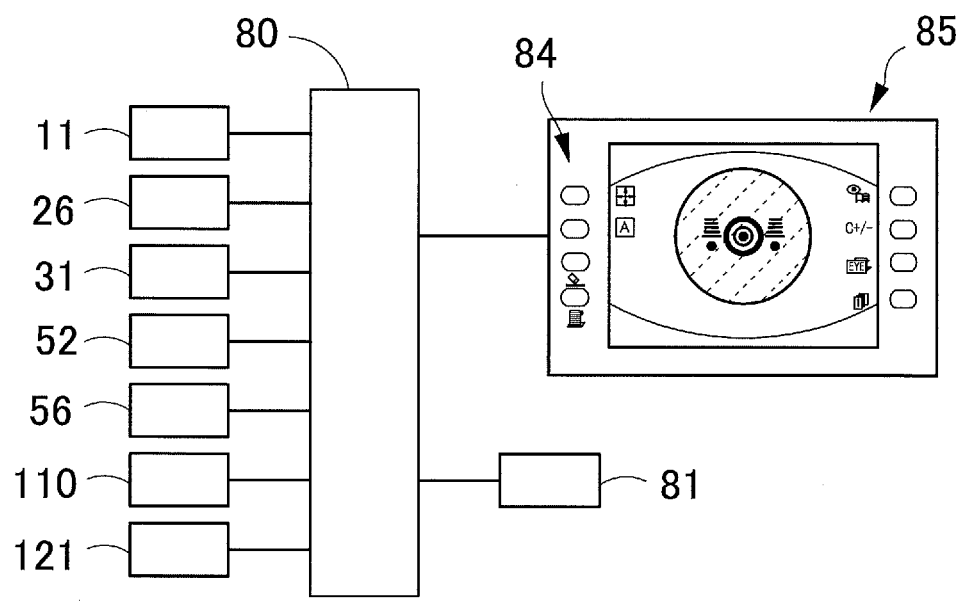
FIG. 8 is a block diagram showing electric and control systems contained in the main unit of the second example.
Figure 9:
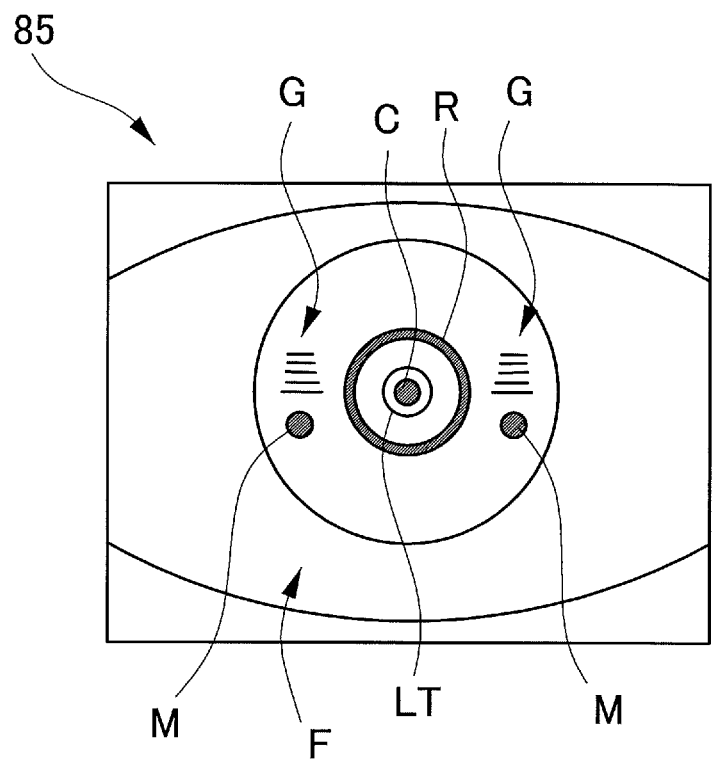
FIG. 9 shows one example of a display screen of a monitor of the second example.
Figure 10:
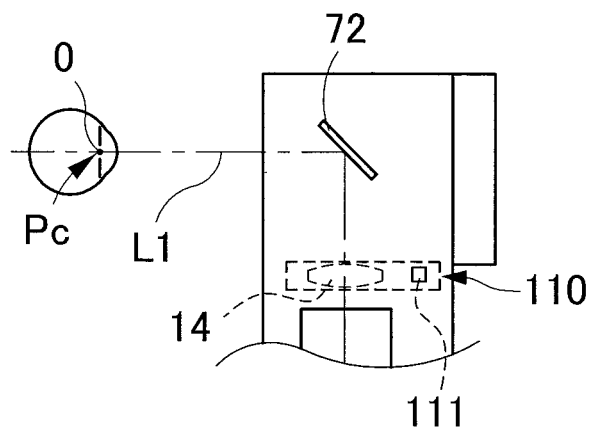
FIGS. 10(*a*) to 10(*c*) are concrete examples to compensate hand shake during measurement in the second example.
Figure 10:
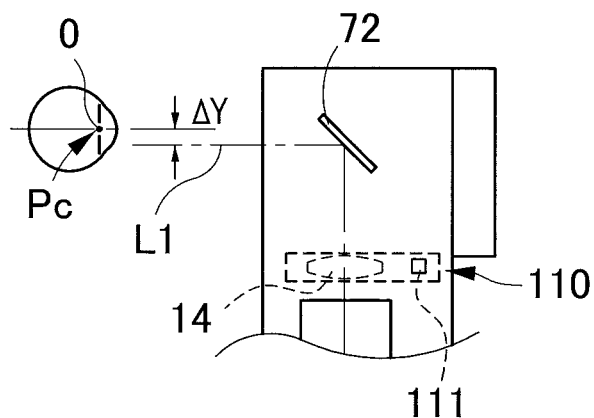
Figure 10:
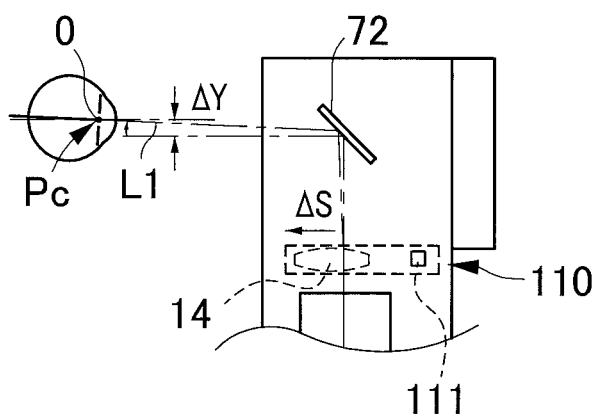

10 Ophthalmoscopic optical system
14 Objective lens

45 First projection optical system
46 Second projection optical system
50 Observation optical system
52 Imaging element
56 PSD
60 Deviation detecting unit
70 Deviation compensating unit
72 Reflection mirror
74 Drive part
100 Main unit
110 Compensating unit
111 Drive part
120 Front projection optical system
150 XY alignment detecting optical system

The invention claimed is:

1. A hand-held ophthalmological device including:
a main unit having an ophthalmoscopic optical system configured to project ophthalmoscopic light to an examinee's eye and receive reflection light therefrom to examine or measure an examinee's eye;
a detector placed in the main unit and configured to detect a relative deviation between an optical axis of the ophthalmoscopic optical system and the examinee's eye;
a deviation compensating optical system placed as a part of the ophthalmoscopic optical system and configured to compensate the deviation; and
a drive part configured to drive the deviation compensating optical system based on output from the detector.

2. The hand-held ophthalmological device according to claim 1, wherein the detector includes a shift deviation detector configured to detect a shift deviation which is applied to the main unit.

3. The hand-held ophthalmological device according to claim 1, wherein the detector receives reflection light from a cornea of the examinee's eye to detect the relative deviation between the optical axis of the ophthalmoscopic optical system and the examinee's eye.

4. The hand-held ophthalmological device according to claim 1, wherein the deviation compensating optical system is placed in a common optical path of a light projecting system and a light receiving system of the ophthalmoscopic optical system or is placed in each of the light projecting system and the light receiving system of the ophthalmoscopic optical system.

5. The hand-held ophthalmological device according to claim 1, wherein
the main unit further includes an imaging optical system having an imaging element configured to capture a front image of the examinee's eye, and
the deviation compensating optical system is placed in a common optical path of the ophthalmoscopic optical system and the imaging optical system.

6. The hand-held ophthalmological device according to claim 5, wherein the deviation compensating optical system is a light deflection member configured to deflect the ophthalmoscopic light.

7. The hand-held ophthalmological device according to claim 6, wherein the light deflection member is a light reflection member configured to reflect the ophthalmoscopic light toward the examinee's eye.

8. The hand-held ophthalmological device according to claim 7, wherein the ophthalmoscopic optical system is an eye refractive power measuring optical system configured to project a measurement index onto a fundus of the examinee's eye, and receive reflection light from the fundus to measure eye refractive power.

9. The hand-held ophthalmological device according to claim 8, wherein the drive part drives the deviation compensating optical system to bring a measurement region by the eye refractive power measuring optical system onto a pupil of the examinee's eye.

10. The hand-held ophthalmological device according to claim 6, wherein the light deflection member is a lens that transmits the ophthalmoscopic light toward the examinee's eye.

11. The hand-held ophthalmological device according to claim 10, wherein
the ophthalmoscopic optical system is an eye refractive power measuring optical system configured to project a measurement index onto a fundus of the examinee's eye, and receive reflection light from the fundus to measure eye refractive power.

12. The hand-held ophthalmological device according to claim 11, wherein the drive part drives the deviation compensating optical system to bring a measurement region by the eye refractive power measuring optical system onto a pupil of the examinee's eye.

13. The hand-held ophthalmological device according to claim 1, wherein
the detector is an optical position sensor, and
the relative deviation between the optical axis and the examinee's eye is detected based on a light receiving signal from the optical position sensor.

14. A hand-held ophthalmological device including:
an ophthalmoscopic optical system including a light projecting optical system configured to project a measurement index onto an examinee's eye and a light receiving optical system configured to receive reflection light from the examinee's eye through a light receiving element, the reflection light being obtained by the measurement index, the ophthalmoscopic optical system being configured to measure eye optical characteristics of the examinee's eye based on an output signal from the light receiving element;
a detector configured to detect a relative positional displacement between an optical axis of the ophthalmoscopic optical system and an anterior segment of the examinee's eye;
a compensating unit including a drive part and being configured to move a lens placed in an optical path of the ophthalmoscopic optical system in a vertical direction with respect to an optical axis of the lens to compensate the positional displacement; and
a controller configured to control the drive part based on an output from the detector.

15. The hand-held ophthalmological device according to claim 14, wherein the detector optically detects the relative positional displacement between the optical axis of the ophthalmoscopic optical system and the anterior segment of the examinee's eye.

16. The hand-held ophthalmological device according to claim 15, further including a projection optical system configured to form an index image at a nearly corneal apex of the examinee's eye,
wherein the detector is an optical position sensor configured to detect a position of the reflection light obtained by the index image, and
the detector is arranged to detect a relative displacement between an optical axis of the ophthalmoscopic optical system and the examinee's eye in a direction perpendicular to the optical axis of the ophthalmoscopic optical system based on a light receiving signal from the optical position sensor.

17. The hand-held ophthalmological device according to claim 14, further including a computing unit configured to compensate a measurement result of eye optical characteristics of the examinee's eye according to a position of the lens.

18. The hand-held ophthalmological device according to claim 14, wherein the detector detects at least a relative deviation between the optical axis of the ophthalmoscopic optical system and the anterior segment of the examinee's eye.

19. The hand-held ophthalmological device according to claim 14, wherein the lens is an objective lens of the ophthalmoscopic optical system.

20. The hand-held ophthalmological device according to claim 14, wherein when the positional displacement exceeds a predetermined permissible range, the lens is returned to a reference position.

* * * * *